United States Patent [19]

Kemp

[11] Patent Number: 5,528,520
[45] Date of Patent: Jun. 18, 1996

[54] CALIBRATION CIRCUIT FOR CAPACITIVE SENSORS

[75] Inventor: Christopher J. Kemp, Monument, Colo.

[73] Assignee: Ford Motor Company, Dearborn, Mich.

[21] Appl. No.: 351,917

[22] Filed: Dec. 8, 1994

[51] Int. Cl.[6] .................................................. G01L 25/00
[52] U.S. Cl. ................................. 364/571.04; 361/283.1; 73/514.32
[58] Field of Search ......................... 364/571.04, 571.01, 364/571.05–571.08; 361/283.1; 324/658–690; 73/514.32, 718, 1 B–1 D, 304 L

[56] References Cited

U.S. PATENT DOCUMENTS

| | | | |
|---|---|---|---|
| 4,208,625 | 6/1980 | Piso | 324/61 R |
| 4,398,426 | 8/1983 | Park et al. | 73/724 |
| 4,434,665 | 3/1984 | Adolfsson et al. | 73/724 |
| 4,449,409 | 5/1984 | Antonazzi | 73/724 |
| 4,457,179 | 7/1984 | Antonazzi et al. | 73/701 |
| 4,517,622 | 5/1985 | Male | 361/283 |
| 4,624,139 | 11/1986 | Collins | 73/304 C |
| 4,669,052 | 5/1987 | Bianco . | |
| 4,736,629 | 4/1988 | Cole . | |
| 4,820,971 | 4/1989 | Ko et al. . | |
| 4,917,199 | 4/1990 | Loshbough | 177/210 C |
| 4,922,756 | 5/1990 | Henrion . | |
| 4,951,236 | 8/1990 | Kawate et al. | 364/571.01 |
| 5,028,876 | 7/1991 | Cadwell . | |
| 5,103,667 | 4/1992 | Allen et al. . | |
| 5,126,812 | 6/1992 | Greiff . | |
| 5,241,850 | 9/1993 | Kawate | 73/1 D |
| 5,245,873 | 9/1993 | Fathauer et al. | 73/304 C |
| 5,253,510 | 10/1993 | Allen et al. . | |
| 5,337,260 | 8/1994 | Spangler . | |
| 5,345,824 | 9/1994 | Sherman et al. . | |

*Primary Examiner*—James P. Trammell
*Attorney, Agent, or Firm*—Kevin G. Mierzwa; Roger L. May

[57] ABSTRACT

A calibration circuit for a capacitive sensor is disclosed which compensates for any offsets or sensitivity variations of the sensor once the sensor has been calibrated. The circuit uses digital calibration codes determined during calibration. The digital codes are modified and unmodified as inputs to a digital-to-analog converter. The digital-to-analog converter applies the corresponding analog equivalents to the inputs of the sensor in a alternate manner so that the voltages applied to the sensor are balanced around a mirror voltage. The balance around the mirror voltage reduces the electrostatic deflection of the sensor which reduces sensor errors. The output of the sensor is converted to a pulse density signal representative of the output of the sensor.

17 Claims, 2 Drawing Sheets

CALIBRATION CIRCUIT FOR CAPACITIVE SENSORS

BACKGROUND OF THE INVENTION

The invention relates generally to a circuit for converting a signal from a capacitive sensor into a form suitable for digital signal processing. More specifically, the invention is a circuit for compensating for offset and sensitivity variations in the sensor output after the sensor has been calibrated.

Capacitive sensors are used in applications such as accelerometers and pressure sensors. One type of capacitive sensor is manufactured by micromachining a slab of silicon to form a miniature tilt plate suspended above a substrate by torsion arms. The tilt plate has a center of mass offset from the torsion arm axis such that, under conditions of non-zero acceleration perpendicular to the plate, the plate tilts relative to the underlying substrate. The tilt plate is metallized and forms a common electrode for two capacitors. Two metallized regions are formed on the substrate directly beneath the suspended tilt plate and form the other electrodes of two capacitors with the tilt plate electrode. The geometry of the two metallized regions and the tilt plate is such that under acceleration the capacitance of one capacitor increases while the capacitance of the other decreases since the distance between the tilt plate and the metallized regions on the substrate either decreases or increases.

In operation, a capacitive tilt plate sensor connects one capacitor electrode from each capacitor at a common node. The common node provides an output of the sensor and the two remaining electrodes provide inputs to the sensor. If one capacitance value is denoted by $C_A$ and the other capacitance is value $C_B$, then the output of the sensor is given by the formula:

$$\text{Sensor Output} = \frac{C_A - C_B}{C_A + C_B}$$

While the capacitances of $C_A$ and $C_B$ vary somewhat nonlinearly with respect to a acceleration, the above formula is remarkably linear with respect to acceleration.

Bias voltages are supplied to the input terminals of the sensor described above so that the output voltage of the sensor provides an indication of the magnitude of the acceleration. One problem with the above described sensor is that unequal bias voltages cause an electrostatic attraction which can result in a deflection of the tilt plate toward the metallized region below the plate. Electrostatic deflection reduces the accuracy of the sensor by changing the capacitance across the plate and inducing nonlinearities in the output.

It would therefore be desirable to reduce the effect of the electrostatic attraction of the tilt plate, thereby increasing the accuracy of the sensor.

SUMMARY OF THE INVENTION

One object of the present invention is to advantageously provide an accurate circuit for providing input voltages to a sensor so that imbalances in the electrostatic attraction between the plates of the capacitors do not that would otherwise create unwanted deflection of the tilt plate.

The preferred embodiment includes a memory storing a digital calibration code having at least two portions representing previously determined calibration codes and a first switch connected to the memory for switching between the two code portions. A digital-to-analog converter has an input with a first selectable connection configured so that when the first selectable connection is in a first state, the input to the digital-to-analog converter is connected to the first switch. When the first selectable connection is in a second state, the digital-to-analog converter is connected to a code mirror circuit. The digital-to-analog converter also has an output with a second selectable connection to either one of the inputs of the sensor. The code mirror circuit converts the calibration code to a predetermined digital mirror code. A first voltage source has a third selectable connection between one of the two inputs of the sensor. The first voltage source and the output of the digital-to-analog converter are alternately connected to opposite inputs of the sensor.

DETAILED DESCRIPTION OF THE PREFERRED EMBODIMENT

Figure 1:
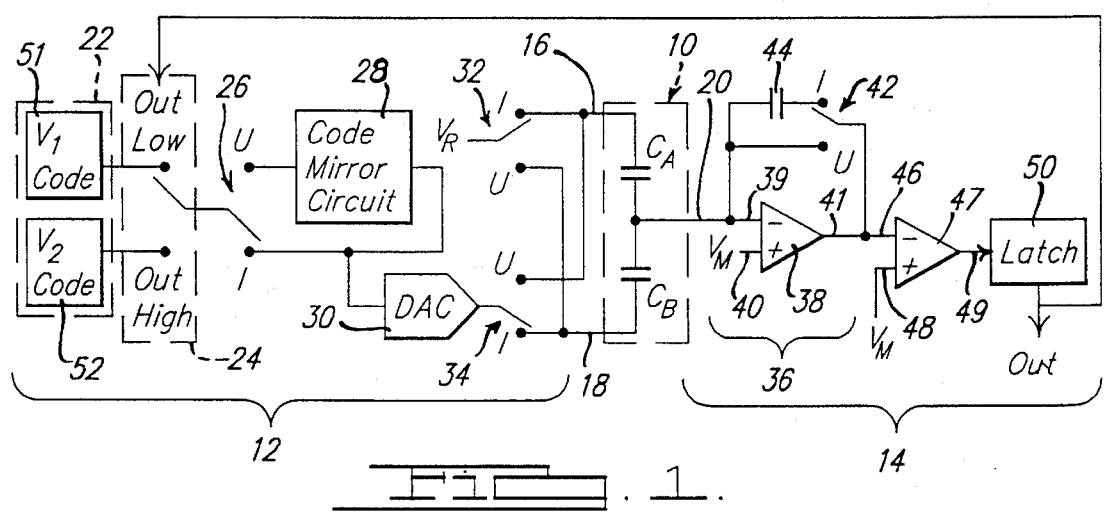
FIG. 1 is a schematic diagram of a calibration circuit according to the present invention.

Referring to FIG. 1, a sensor 10 is connected to an input stage 12 which provides predetermined voltages to sensor 10 in a predetermined manner. An output stage 14 connected to sensor 10 converts the analog sensor output to a corresponding digital pulse density signal representing acceleration for direct input into a microprocessor or other circuitry.

Sensor 10 is formed of two capacitors $C_A$ and $C_B$ connected in series. Input terminals 16 and 18 and output terminal 20 form the electrodes of capacitors $C_A$ and $C_B$. Input stage 12 is connected to input terminals 16 and 18. Output stage 14 is connected to output terminal 20 at the common node between capacitor $C_A$ and $C_B$.

Input stage 12 comprises a memory 22 connected in series with a first switch 24 which gates a portion of memory 22 to a second switch 26. Second switch 26 couples the contents of memory 22 to either code mirror circuit 28 or the input of digital-to-analog converter (DAC) 30. A third switch 32 and a fourth switch 34 are used to apply either the output of DAC 30 or a voltage source $V_R$ alternately to each of input terminals 16 and 18 of sensor 10.

Output stage 14 comprises an integrator 36 which is preferably formed of an operational amplifier 38 having its inverting input terminal 39 connected to the output terminal 20 of sensor 10. Operational amplifier 38 has a noninverting input 40 connected to a predetermined voltage source $V_M$. Operational amplifier 38 has an output terminal 41 and a feedback loop connected to its inverting input terminal 39. The feedback loop comprises a fifth switch 42 which either connects output terminal 41 directly to inverting terminal 39 or connects a feedback capacitor 44 between output terminal 41 and inverting terminal 39 to perform the integrate function.

Output terminal 41 of operational amplifier 38 is connected to an inverting terminal 46 of a comparator 47. Comparator 47 has a noninverting terminal 48 connected to a voltage source $V_M$. Comparator 47 has an output terminal 49 which provides a digital output representing the polarity of inverting terminal 46 in relation to noninverting terminal 48. Output terminal 49 is connected in series to a latch 50 which maintains a digital output for coupling to a microprocessor or other circuitry.

Memory 22 is preferably a nonvolatile memory such as EEPROM, fuse-blowing memory or zener-zapping memory. Memory 22 has two code portions which store calibration voltages $V_1$ and $V_2$ in digital form. The calibration voltages are derived in a known calibration process for the type of sensor used. If the sensor is an accelerometer, the calibration voltages are derived in a centrifuge. The bit length of the stored calibration codes is preferably the same. The bit length determines the resolution of the offset and sensitivity calibration.

First switch 24 and second switch 26 are preferably conventional digital multiplexors. First switch 24 selects one of the calibration codes $V_1$ or $V_2$ for input to second switch 26. First switch 24 is connected to the output of latch 50 which holds the output of the comparator at the end of a previous clock cycle. If the output was low, first switch 24 passes $V_1$. If the output was high, first switch 24 passes $V_2$.

Figure 2:
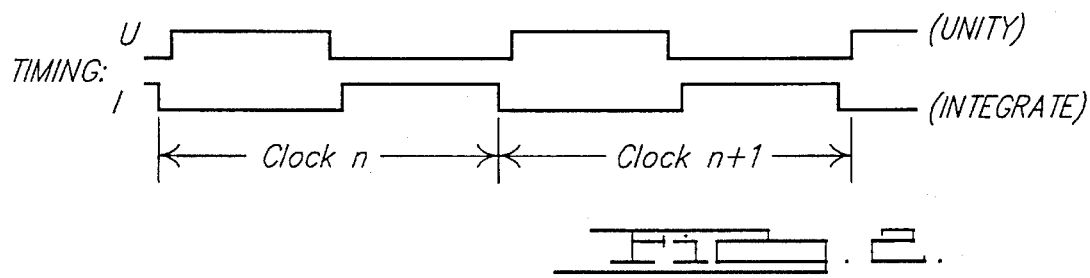
FIG. 2 is a timing diagram showing clock signals used in the schematic of FIG. 1.

Referring now to FIGS. 1 and 2, third switch 32, fourth switch 34 and fifth switch 42 are preferably conventional CMOS switches. The switches, operational amplifier and comparator may all be fabricated on a single integrated circuit. CMOS is preferred in the fabrication of the circuitry since CMOS provides excellent analog switches, essentially zero DC input current for the operational amplifier and the comparator, and good capacitor matching. The switches are controlled according to clock signal as shown in FIG. 2. The two clock signals, unity and integrate, are preferably derived from a single clock oscillator in a conventional manner. The two clock signals are timed so that only one of either unity or integrate is high in a non-overlapping manner. Switches 26, 32, 34 and 42 are controlled by whichever clock signal is high. When the unity clock is high, the switches are connected to the "U" pin and when the integrate clock goes high the switches are connected to the "I" pin.

Code mirror circuit 28 is configured to modify the input digital code representative of the voltage $V_1$ so that a modified digital code is applied to the DAC 30. If the $V_1$ code is being applied to the code mirror circuit, the code mirror circuit modifies the $V_1$ code so that the output of DAC 30 is $V_{1M}$ which is defined as $(2V_M-V_1)$. $V_M$ is generated within the DAC 30 and will be further described below. The formula for $V_{1M}$ can be rewritten as $(V_1-V_M)=(V_M-V_{1M})$. From this formula it is evident that the voltage $V_{1M}$ is either as many volts below $V_M$ as $V_1$ is above $V_M$, or as many volts above $V_M$ as $V_1$ is below $V_M$. The same is true with respect to $V_2$, i.e., $(V_2-V_M)=(V_M-V_{2M})$. From this it follows that the DC electrostatic attraction on the $C_A$ side of the plate is identical to that on the $C_B$ side of the plate.

Figure 3:
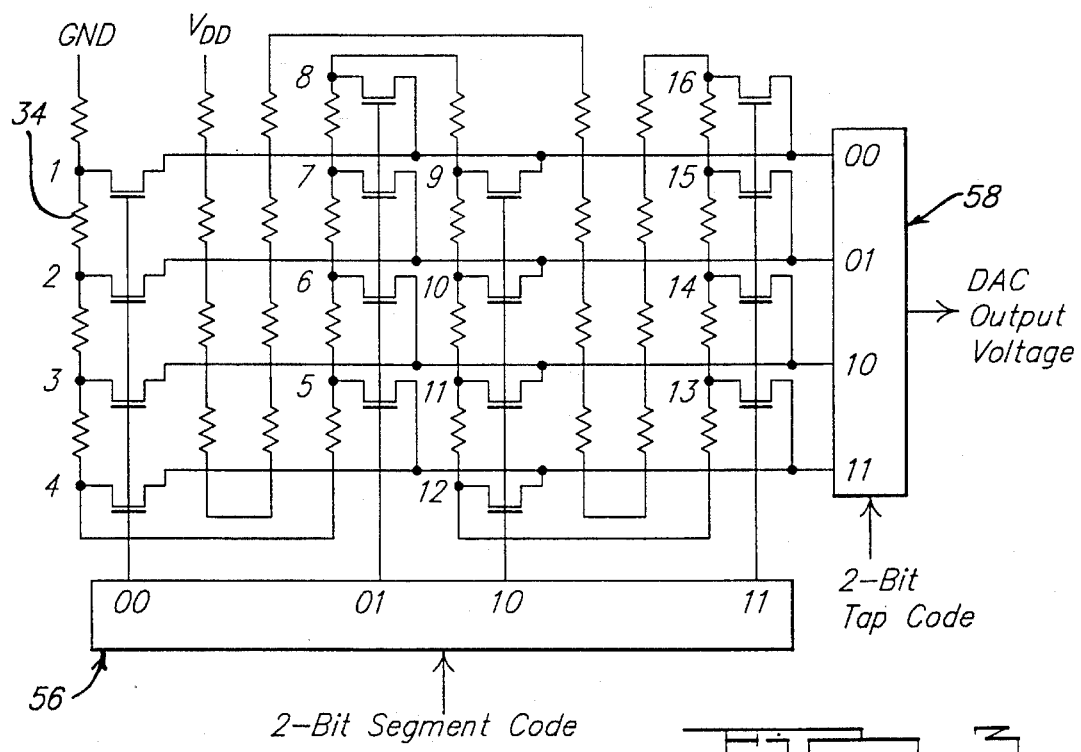
FIG. 3 is a detailed schematic of the digital-to-analog converter of FIG. 1.
Figure 4A:
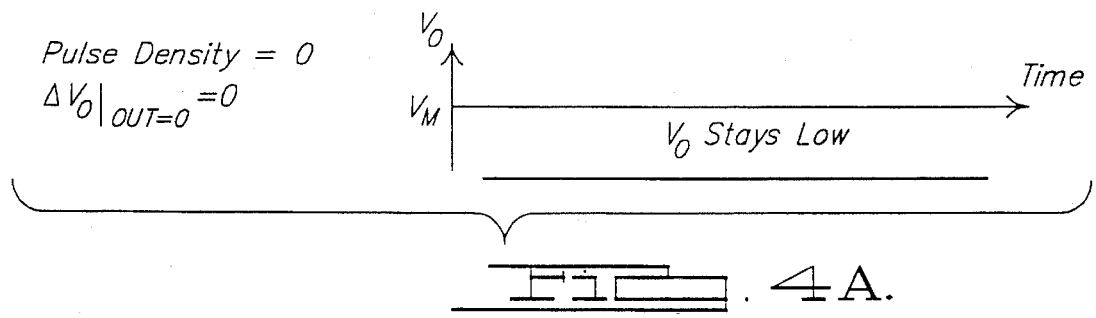
FIGS. 4A–4E plot output voltage versus time for the analog $V_o$ output of the integrator in FIG. 1.
Figure 4B:
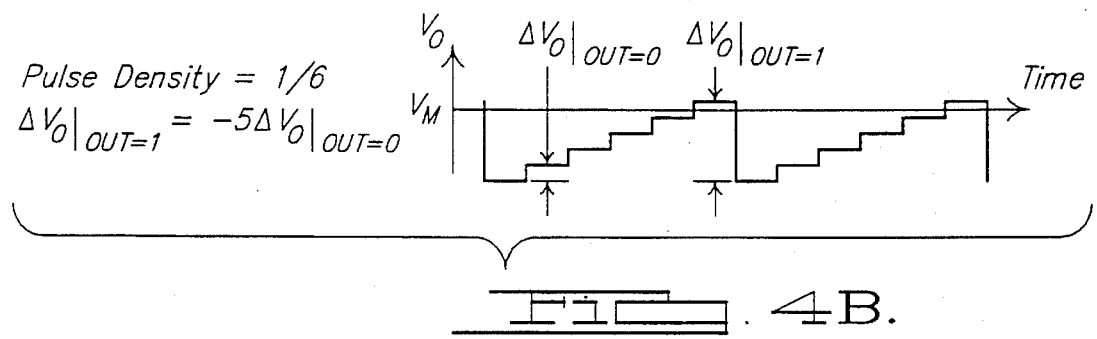
Figure 4C:
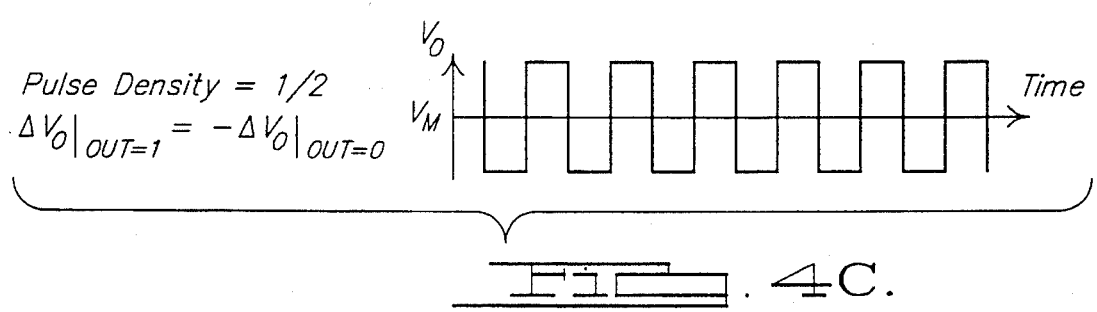
Figure 4D:
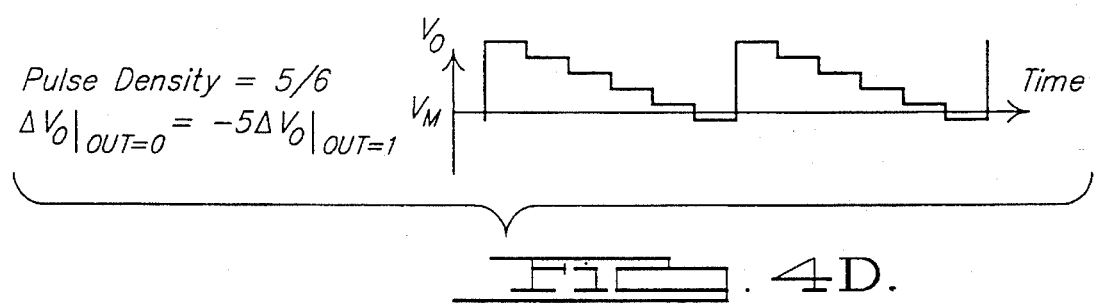
Figure 4E:
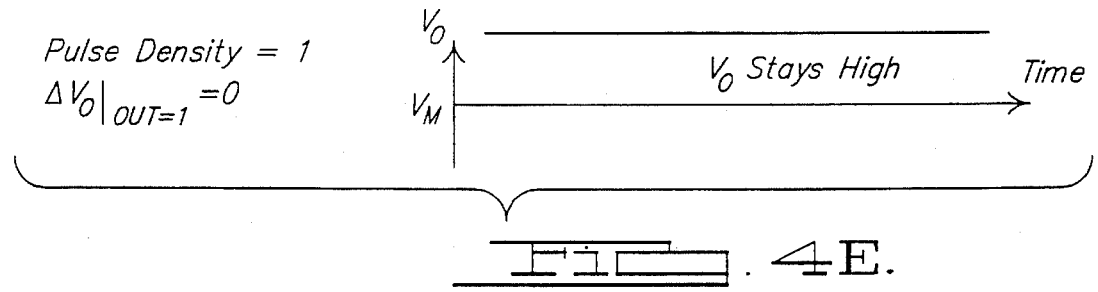

Referring now to FIG. 3, the operation of DAC 30 will be described. DAC 30 consists of several equal valued resistors 34 connected in series between a supply voltage and ground. For simplicity, only 32 resistors are shown, however in practice there may be 1024 or more. The resistor string is formed into a double serpentine structure to gain the benefits of cancellation of thermal gradients and for ease of access to the tap points which are numbered 1–16. The resistor string shown has 8 segments of 4 resistors. The tap points numbered 1–16 are used from ground to half the supply voltage, (i.e., the bottom four segments are used). To access the tap points, part of the digital code called the segment code is used to select all the tap points of the chosen segment via a segment decoder 56. The segment code is preferably the first group of significant bits. The remaining bits called the tap code are supplied to an analog multiplexor 58 which selects the correct tap point within the selected segment and delivers its voltage to the DAC output. In a conventional DAC, the tap code that is supplied to analog multiplexor 58 is inverted for odd segments only so that the DAC voltage increases monotonically by one significant bit each time the digital code is incremented by one. Without the inversion, the DAC voltage would not increase monotonically. For the present invention the inversion is removed.

As an example, the mirror voltage $V_M$ is the voltage half way between the voltages on tap points 8 and 9 (i.e., 1.328125 V if the supply voltage is 5 V). If OUT is low and the integrate clock is high, the $V_1$ code is unmodified. If, for example, $V_1$ is 1110, tap point 14 (2.1875 V) is delivered to the DAC output as $V_1$. If Unity is high, the segment code is inverted so that 0010 is applied to the DAC. Tap point 3 (0.46875 V) is delivered to the DAC output as $V_{1M}$. $V_1$ and $V_{1M}$ are symmetrically located about the mirror voltage $V_M$ as desired.

The mirror voltage $V_M$ is used to provide the noninverting input 40 of the operational amplifier 38 and the noninverting input 48 of comparator 47. But, the voltage between tap points 8 and 9 is not directly available for this purpose. However, when 1024 resistors and a 5 V supply voltage are used, for example, the error for in choosing either adjacent tap point results in only a 0.0025 V error. Such a small error has been found insignificant in the electrostatic charge balance.

The operation of the circuit is best understood by understanding the sequence of events which occur during each clock cycle. In the unity phase during clock cycle n in FIG. 2, the output of latch 50 is either high or low during both phases of clock cycle n depending on the comparator output at the falling edge of the previous clock cycle n−1 (not shown). If, for example, the latch output is low, the bits of $V_1$ are passed through first switch 24. $V_1$ is routed to the code mirror circuit. DAC 30 places voltage $V_{1M}$ at input terminal 16 of sensor 10. Reference voltage $V_R$ is placed on input terminal 18 of sensor 10. By the end of the unity phase, all the voltages settle to a static state. No integration takes place at operational amplifier 38.

During the integrate phase of clock cycle n, $V_1$ is fed directly to DAC 30. The voltage change at input terminal 18 from the unity phase to the integrate phase is given by the formula $(V_1-V_R)$. Reference voltage $V_R$ is now placed on input terminal 16 of sensor 10. The voltage change at input terminal 16 is $(V_R-V_{1M})$. Operational amplifier 38 is now configured as an integrator. From these changes it follows that the change in the charge Q on feedback capacitor 44 is given by the formula:

$$\Delta Q = C_A(V_R-V_{1M}) + C_B(V_1-V_R)$$

The total charge on feedback capacitor 44 is the change in charge above plus the residual charge from prior clock cycles. The change in the voltage $V_0$ at output terminal 41 of operational amplifier 38 is given by the formula:

$$\Delta V_o = \frac{\Delta Q}{C_{44}}$$

If $V_o$ remains less than $V_M$ at the end of the integrate phase, the output of latch 50 will continue to be latched low for the next clock cycle n+1. If $V_o$ is greater than $V_M$, the output of latch 50 will be latched high for the next clock cycle n+1.

In the unity phase during clock cycle n+1 in FIG. 2, assume that the output of latch 50 is high. If the latch is high, the bits of $V_2$ are passed through first switch 24. $V_2$ is routed to the code mirror circuit. DAC 30 places voltage $V_{2M}$ at input terminal 16 of sensor 10. Reference voltage $V_R$ is placed on input terminal 18 of sensor 10. By the end of the unity phase all the voltages settle to a static state. No integration takes place at operational amplifier 38.

During the integrate phase of clock cycle n+1, $V_2$ is fed directly to DAC 30. The voltage change at input terminal 18 from the unity phase to the integrate phase is given by the formula $(V_2-V_R)$. Reference voltage $V_R$ is now placed on input terminal 16 of sensor 10. The voltage change at input terminal 16 is $(V_R-V_{2M})$. Operational amplifier 38 is now configured as an integrator. From these changes it follows that the change in charge Q on feedback capacitor 44 is given by the formula:

$$\Delta Q = C_A(V_R - V_{2M}) + C_B(V_2 - V_R)$$

The total charge on feedback capacitor 44 is the change in charge above plus the residual charge from prior clock cycles. The change in the voltage at output terminal 41 of operational amplifier 38 is given by the formula:

$$\Delta V_o = \frac{\Delta Q}{C_{44}}$$

If $V_o$ remains greater than $V_M$ at the end of the integrate phase, the output of latch 50 will continue to be latched high for the next clock cycle n+2. If $V_o$ is less than $V_M$, the output of latch 50 will be latched low for the next clock cycle n+2.

From the above equations, it follows that the formula for the change in $V_o$ for a given clock cycle depends on the value of the output of latch 50 for that cycle as follows:

$$\Delta V_o(whenOUT=0) = \frac{C_A(V_R - V_{1M}) + C_B(V_1 - V_R)}{C_{44}}$$

$$\Delta V_o(whenOUT=1) = \frac{C_A(V_R - V_{2M}) + C_B(V_2 - V_R)}{C_{44}}$$

The values of these $V_o$ changes are significant in that their ratio determines the pulse density of the circuit as shown in FIG. 4. The fractional pulse density FPD is defined as the number of clock periods per second having a high output value at latch 50, divided by the clock frequency. The useful FPD range of the device is between 0 and 1. In this range $\Delta V_o$ (when OUT=0) is positive while $\Delta V_o$(when OUT=1) is negative. Thus, $V_o$ always moves in the direction of $V_M$ in any given clock cycle.

The FPD is related to the ratio of $V_o$ changes as follows:

$$FPD = \frac{1}{1 - \left[\frac{\Delta V_o(whenOUT=1)}{\Delta V_o(whenOUT=0)}\right]}$$

By inserting the two equations prior to the FPD equation into the FPD equation and with some manipulation and using the fact that $V_{1M}=(2V_M-V_1)$ and $V_{2M}=(2V_M-V_2)$, the equation for fractional pulse density follows:

$$FPD = \left[\frac{1}{2} + \frac{\frac{V_1+V_2}{2} - V_M}{V_1 - V_2}\right] + \left[\frac{V_R - V_M}{V_1 - V_2}\right]\left[\frac{C_A - C_B}{C_A + C_B}\right]$$

The FPD is written in the form:

$$FPD = B + G\left[\frac{C_A - C_B}{C_A + C_B}\right]$$

The sensitivity calibration term is G and the offset term is B. It should be noted that the sensitivity and offset terms depend only on the calibration voltages $V_1$ and $V_2$ and the fixed voltages $V_M$ and $V_R$. The bracketed term as noted above is the output of the sensor.

The digital pulse density signal is used as an input to a microprocessor or other signal processing circuitry. Such a signal is used, for example, in the determination of whether to deploy an airbag.

As would be evident to one skilled in the art, several modifications of the invention may be made while still being within the scope of the appended claims. For example, the sensor can also be configured as a pressure sensor configuration by fixing one of the two sensor capacitors while allowing the other to vary.

What is claimed is:

1. A circuit for calibrating a capacitive sensor having two inputs and an output comprising:

a memory storing at least two digital calibration codes;

a first switch means connected to said memory for switching between said two code portions;

a digital-to-analog converter having an input, said input having a first selectable connection so that when said first selectable connection is in a first state, said digital-to-analog converter is connected to said first switch and when said first selectable connection is in said second state, said digital-to-analog converter is connected to a code mirror circuit, said digital-to-analog converter having an output with a second selectable connection to one of said inputs of said sensor;

said code mirror circuit converting said calibration code to a predetermined digital mirror code; and a first voltage source having a third selectable connection between one of said two inputs of said sensor;

wherein said first voltage source and said output of said digital-to-analog converter are alternately connected to opposite inputs of said sensor.

2. A circuit for calibrating a capacitive sensor as recited in claim 1 wherein said first, second and third selectable connections each comprise a respective switch.

3. A circuit for calibrating a capacitive sensor as recited in claim 2 further comprising a clock coupled to each of said first, second and third selectable connections for operating said first, second and third selectable connections synchronously between a first state and a second state.

4. A circuit for calibrating a capacitive sensor as recited in claim 3 wherein said clock generates two non-overlapping signals.

5. A circuit for calibrating a capacitive sensor as recited in claim 1 wherein the state of said first switch means is responsive to the polarity of the output.

6. A circuit for calibrating a capacitive sensor as recited in claim 1 further comprising pulse density output means connected to said sensor for converting said sensor output to a pulse density modulated digital signal.

7. A circuit for calibrating a capacitive sensor as recited in claim 6 wherein said pulse density output means includes an integrator, a comparator and a latch.

8. A circuit for calibrating a capacitive sensor as recited in claim 1 wherein said digital-to-analog converter comprises a simplified resistor string.

9. A circuit for calibrating a capacitive sensor as recited in claim 1 wherein said calibration codes have the same number of bits.

10. A circuit for calibrating a capacitive sensor as recited in claim 1 wherein said memory is nonvolatile.

11. A circuit for calibrating a capacitive sensor as recited in claim 1 wherein said nonvolatile memory is an EEPROM.

12. A circuit for calibrating a capacitive sensor having two inputs and an output comprising:

a memory storing at least two digital calibration codes;

a clock;

a first switch connected to said memory for switching between said two code portions;

a digital-to-analog converter having an input, said input having a second switch so that when said second switch is in a first state, said digital-to-analog converter is connected to said first switch and when said second switch is in said second state, said digital-to-analog converter is connected to a code mirror circuit, said digital-to-analog converter having an output with a third switch connected to one of said inputs of said sensor;

said code mirror circuit converting said calibration code to a predetermined digital mirror code;

a first voltage source having a fourth switch between one of said two inputs of said sensor;

an integrator having a feedback loop including a fifth switch and a capacitor;

a comparator connected to said integrator outputting a pulse density modulated signal; and wherein each of said second, third, fourth and fifth switches are connected to said clock for operating said second, third, fourth and fifth switches synchronously between a first state and a second state.

13. A circuit for calibrating a capacitive sensor as recited in claim 12 wherein said clock generates two non-overlapping signals.

14. A circuit for calibrating a capacitive sensor as recited in claim 12 wherein said first voltage source and said output of said digital-to-analog converter are alternately connected to opposite inputs of said sensor.

15. A circuit for calibrating a capacitive sensor as recited in claim 12 wherein said integrator including an operational amplifier having two inputs, one input connected to an output of the sensor, a second input to a second voltage source.

16. A circuit for calibrating a capacitive sensor as recited in claim 12 wherein said comparator is connected to said second voltage source.

17. A circuit for calibrating a capacitive sensor as recited in claim 12 wherein said calibration codes have the same number of bits.

* * * * *